United States Patent
Schwarz

(10) Patent No.: US 10,080,906 B2
(45) Date of Patent: *Sep. 25, 2018

(54) METHODS AND DEVICES FOR TISSUE TREATMENT USING MECHANICAL STIMULATION AND ELECTROMAGNETIC FIELD

(71) Applicant: BTL HOLDINGS LIMITED, Nicosia (CY)

(72) Inventor: Tomáš Schwarz, Prague (CZ)

(73) Assignee: BTL Holdings Limited, Nicosia (CY)

( * ) Notice: Subject to any disclaimer, the term of this patent is extended or adjusted under 35 U.S.C. 154(b) by 0 days.

This patent is subject to a terminal disclaimer.

(21) Appl. No.: 15/471,946

(22) Filed: Mar. 28, 2017

(65) Prior Publication Data

US 2017/0209708 A1 Jul. 27, 2017

Related U.S. Application Data

(63) Continuation-in-part of application No. 14/870,713, filed on Sep. 30, 2015, now Pat. No. 9,636,516.

(51) Int. Cl.

| | |
|---|---|
| *A61H 9/00* | (2006.01) |
| *A61H 19/00* | (2006.01) |
| *A61H 23/00* | (2006.01) |
| *A61H 23/02* | (2006.01) |
| *A61N 2/00* | (2006.01) |
| *A61N 5/06* | (2006.01) |
| *A61N 2/02* | (2006.01) |
| *A61N 5/067* | (2006.01) |

(Continued)

(52) U.S. Cl.
CPC .............. *A61N 2/002* (2013.01); *A61H 9/005* (2013.01); *A61H 23/008* (2013.01); *A61H 23/0245* (2013.01); *A61N 2/004* (2013.01); *A61N 2/02* (2013.01); *A61N 5/0625* (2013.01); *A61B 2018/00464* (2013.01); *A61H 9/0028* (2013.01); *A61H 9/0057* (2013.01); *A61H 19/00* (2013.01); *A61H 21/00* (2013.01); *A61H 2201/0165* (2013.01); *A61H 2201/025* (2013.01); *A61H 2201/0207* (2013.01); *A61H 2201/0214* (2013.01); *A61H 2201/0228* (2013.01);

(Continued)

(58) Field of Classification Search
CPC .... A61H 9/0007; A61H 9/005; A61H 9/0071; A61H 23/008; A61N 5/06–2005/073; A61B 17/225–2017/2253
See application file for complete search history.

(56) References Cited

U.S. PATENT DOCUMENTS

| | | | | |
|---|---|---|---|---|
| 3,163,161 A | * | 12/1964 | Courtin | A61H 9/0071 601/159 |
| 5,143,063 A | * | 9/1992 | Fellner | A61N 1/40 128/897 |

(Continued)

OTHER PUBLICATIONS

Gerdesmeyer, L., et al., Radial Extracorporeal Shockwave Therapy (rESWT) in Orthapaedics. J. Minerals. (4 pages) Munich, Germany. 11(4): 36-39; 2004.

*Primary Examiner* — Valerie L Woodward
(74) *Attorney, Agent, or Firm* — Kenneth H. Ohriner; Perkins Coie LLP

(57) ABSTRACT

Devices and methods for tissue treatment produce a mechanical stimulation therapy and electromagnetic field therapy. The mechanical stimulation therapy provides stimulation of blood circulation and stimulates treated cells. The electromagnetic field enables thermal treatment of tissue. Combination of both therapies improves soft tissue treatment, mainly connective tissue in the skin area and fat reduction.

29 Claims, 6 Drawing Sheets

(51) Int. Cl.
    *A61N 5/02*     (2006.01)
    *A61H 21/00*     (2006.01)
    *A61B 18/00*     (2006.01)

(52) U.S. Cl.
    CPC .. *A61H 2201/0242* (2013.01); *A61H 2201/10* (2013.01); *A61H 2201/5007* (2013.01); *A61H 2201/5028* (2013.01); *A61H 2201/5043* (2013.01); *A61H 2201/5061* (2013.01); *A61H 2201/5064* (2013.01); *A61H 2201/5082* (2013.01); *A61H 2201/5092* (2013.01); *A61H 2207/00* (2013.01); *A61N 5/022* (2013.01); *A61N 2005/067* (2013.01); *A61N 2005/0651* (2013.01); *A61N 2005/0659* (2013.01); *A61N 2005/0662* (2013.01)

(56) References Cited

U.S. PATENT DOCUMENTS

| | | | |
|---|---|---|---|
| 6,605,080 B1 * | 8/2003 | Altshuler | A61B 18/203 606/13 |
| 2004/0073079 A1 * | 4/2004 | Altshuler | A61B 5/6843 600/1 |
| 2004/0171970 A1 | 9/2004 | Schleuniger et al. | |
| 2005/0049543 A1 | 3/2005 | Anderson et al. | |
| 2008/0009885 A1 * | 1/2008 | Del Giglio | A61B 17/22012 606/128 |
| 2008/0228520 A1 | 9/2008 | Day et al. | |
| 2008/0312647 A1 | 12/2008 | Knopp et al. | |
| 2009/0248004 A1 * | 10/2009 | Altshuler | A61B 18/18 606/33 |
| 2011/0046523 A1 | 2/2011 | Altshuler et al. | |
| 2012/0029394 A1 | 2/2012 | Babaev | |
| 2012/0150079 A1 | 6/2012 | Rosenberg | |
| 2013/0178764 A1 | 7/2013 | Eckhouse et al. | |
| 2013/0303904 A1 * | 11/2013 | Barthe | A61B 8/0858 600/439 |
| 2014/0303525 A1 | 10/2014 | Sitharaman | |
| 2014/0350438 A1 | 11/2014 | Papirov et al. | |
| 2015/0141877 A1 | 5/2015 | Feldman | |
| 2015/0165238 A1 | 6/2015 | Slayton et al. | |
| 2016/0016013 A1 | 1/2016 | Capelli et al. | |

* cited by examiner

METHODS AND DEVICES FOR TISSUE TREATMENT USING MECHANICAL STIMULATION AND ELECTROMAGNETIC FIELD

PRIORITY CLAIM

This Application is a Continuation-in-part of U.S. patent application Ser. No. 14/870,713 filed Sep. 30, 2015, and now pending, which is incorporated by reference herein in its entirety.

FIELD OF THE INVENTION

The invention relates to method and device for soft tissue treatment, mainly connective tissue in the skin area and fat reduction.

BACKGROUND OF THE INVENTION

Human skin is tissue which is commonly treated in order to improve its visual appearance. Skin is composed of three basic elements: the epidermis, the dermis and the hypodermis or so called subcutis. The outer and also thinnest layer of skin is the epidermis. Epidermis contains mainly stratified squamous epithelium of which the outer side keratinizes and ensures coverage whereas the inner side contains a pigment. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT).

SWAT is formed by aggregation of fat cells ranging up to 120 microns in diameter and containing as much as 95% glycerides and fatty acids by volume. Overeating and unhealthy lifestyles may result in an increase of size and/or number of the fat cells. The fat cells create lobules which are bounded by connective tissue, fibrous septa (retinaculum cutis).

Another part of adipose tissue is located in peritoneal cavity and is known as abdominal obesity. Visceral fat layer forming visceral white adipose tissue (VWAT) is located between parietal peritoneum and visceral peritoneum, closely below muscle fibers adjoining the hypodermis layer.

Excess of adipose tissue in subcutaneous or abdominal area may be perceived as aesthetically undesirable, mainly in the buttocks, thighs, abdomen or hips, where even weight loss after dieting and exercise may not lead to satisfactory results. Moreover, in the last few decades, more people suffer from growth of visceral white adipose tissue (VWAT) mainly in their abdominal area. Visceral fat has been also linked to various cardiovascular diseases and diabetes.

The undesirable topographic skin appearance may also be caused by changes in dermal or sub-dermal layer of the skin, especially by excessive number or volume of fat cells, weakening of fibrous septas, loss of elasticity and/or limited lymph flow, which may result in accumulation of toxins.

Mechanical stimulation includes acoustic, ultrasound and/or shock waves. Shock waves are waves characterized by steep pressure amplitude growth in comparison to the surrounding pressure. Despite their relationship with other types of mechanical stimulation, shock waves are different mainly in pressure magnitude and shape of the pressure wave. In comparison to ultrasound waves where the pressure periodically oscillates with limited bandwidth and amplitude, shock waves are characterized by non-linearity during the wave propagation. In the present invention, shock wave propagation is characterized by swift positive pressure increase in the range from one nanosecond up to 100 microseconds with positive peak pressure amplitudes up to 150 MPa. In comparison, regular ultrasound methods have positive peak pressure amplitudes up to about 3 MPa. The pulse duration (based on the time the pressure exceeds a half value of peak positive pressure) is preferably in the range of hundreds of nanoseconds to 10-100 of microseconds.

There are four main principles for generating shock waves: electrohydraulic, piezoelectric, electromagnetic and ballistic. The shock waves produced by electrohydraulic principle, piezoelectric principle or electromagnetic principle are traditionally used for destruction of calculi e.g. kidney stones. As these shock waves are focused, they may be characterized as hard shock waves because the energy is directed into small point in the tissue.

The ballistic shock waves have a naturally non-focused/radial propagation. Radial/non-focused propagation is characterized by smooth propagation.

Various non-invasive methods for skin treatment containing light, radiofrequency, microwave, and ultrasound treatment has been previously developed. Nevertheless, improved treatments in aesthetic medicine are needed.

SUMMARY OF THE INVENTION

Methods and devices for a non-invasive treatment of soft tissue including SWAT, VWAT and connective tissue use a mechanical stimulation and electromagnetic field therapy. Methods and devices provide a non-invasive treatment of soft tissue by an electromagnetic field and a mechanical stimulation, which may be an acoustic, ultrasound or shock wave. Methods and devices provide a massage of tissue. The mechanical stimulation may be generated by electrohydraulic, piezoelectric and/or electromagnetic techniques, or pneumatically (including ballistic principle).

A ballistic mechanism of shock wave generation may be used. The ballistic shock wave mechanism contains a projectile striking against an applicator head for generating the shock wave. The ballistic shock wave have a naturally non-focused, planar or moderately focused propagation. Ballistic shock wave methods of propagation are characterized by smooth propagation. Also other non-focused, radial or moderately focused methods may be used. However, methods and devices may also use focused ballistic shock waves, wherein the shock wave may be focused by the shape of a percussion guide.

The electromagnetic field may be generated by energy delivery elements (e.g. LED, lamps, and a bipolar, monopolar, unipolar, multipolar electrodes) in direct, indirect or even noncontact arrangement with the skin surface. The electromagnetic field frequency may be in the range from 0.1 MHz to 10 GHz.

The electromagnetic field may be generated by a laser diode module or a LED. The electromagnetic field wavelength may be preferably in the range from 600 nm to 1200 nm.

Combinations of both therapies provide new soft tissue treatment with reduced risk of adverse effects. Treatment may lead to remodeling of a soft tissue in the skin area including white adipose tissue. Remodeling may include reduction in number and/or volume of the visceral white adipose tissue and/or the subcutaneous white adipose tissue. Treatment may also lead to improvement of connective tissue elasticity, mainly elasticity of fibrous septae connecting the dermis to underlying fascia.

Although neocollagenesis is normally induced at temperatures higher than 48° C., the combination of mechanical stimulation and an electromagnetic field enables improved results at lower temperatures and with less stress of the tissue. Temperature of the soft tissue during the treatment may be about 32-48° C.

According to another embodiment the temperatures may reach above 50° C. which leads to thermal denaturation of collagen and collagen shrinkage.

The sum of the energy flux density of the mechanical stimulation and the electromagnetic field applied to the patient simultaneously, successively or in overlap is typically above 1 mW·mm$^{-2}$. With the simultaneous method, the electromagnetic field and mechanical stimulation are both used simultaneously during the time interval e.g., 1-10 seconds. In the successive method, an electromagnetic field is used during a first time interval of e.g., 1-5 seconds. The electromagnetic field is then stopped and mechanical stimulation is used in a subsequent time interval of e.g., 6-10 (immediately afterwards the electromagnetic field ends, with the combined application time in this example totaling to 10 seconds). In the overlapping method, an electromagnetic field is used during a first time interval from e.g., 1-7 seconds, and mechanical stimulation is used in a second overlapping time interval of e.g., 4-10 seconds (wherein during the second time interval the electromagnetic field and mechanical stimulation are simultaneously applied over the second interval starting at 4 seconds and ending at 7 seconds).

In comparison with known techniques, the present device and method enable gentle treatment with no surgery and reduced amounts of energy delivered into the tissue.

The present methods and device may provide improved soft tissue treatment, mainly in skin region such improving skin laxity, skin tightening, wrinkles reduction and including fat cells elimination.

GLOSSARY

"lipolysis" includes apoptosis and/or necrosis of the targeted adipocytes.

"shockwave" is characterized by swift positive pressure increase in the range from ones of nanoseconds up to tens of microseconds with positive peak pressure amplitudes up to 150 MPa. The pulse duration (based on the time the pressure exceeds a peak positive pressure/2) is approximately in the range of hundreds of nanoseconds to tens of microseconds.

"soft tissue remodeling" or "remodeling of soft tissues" means reorganization or renovation of existing tissue with improvement of its elasticity and visual appearance, including reduction of white adipose tissue in number and/or volume.

"massage" means the change of pressure applied onto the tissue related to ambient pressure.

DETAILED DESCRIPTION

Figure 1:
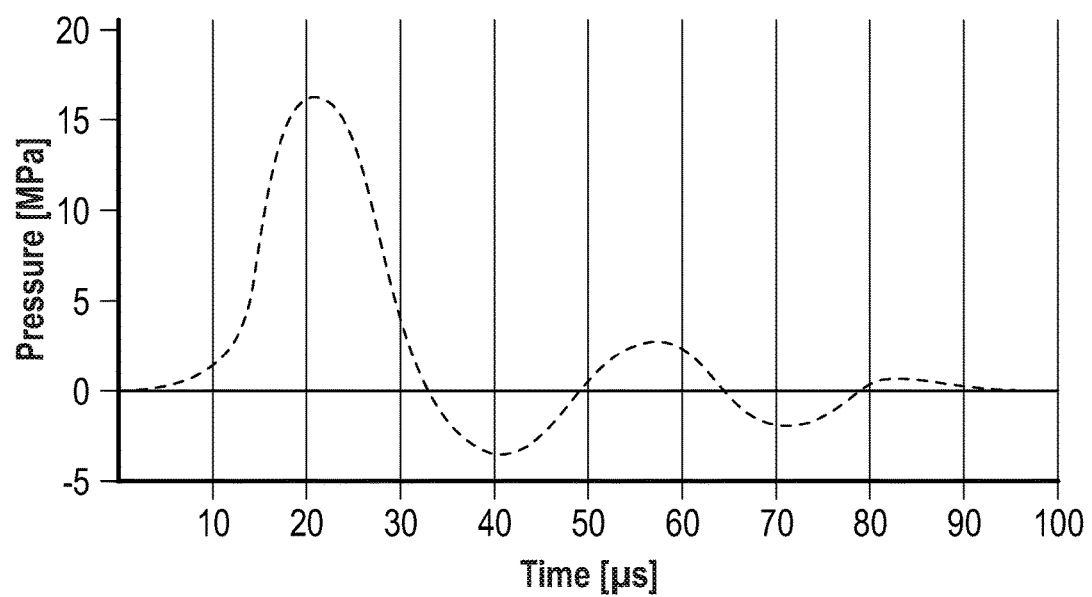
FIG. 1 is a graph of an example of a mechanical stimulation propagation.

FIG. 1 shows an example of mechanical stimulation propagation. Mechanical stimulation e.g. shock waves are characterized by steep pressure amplitude growth in comparison to the surrounding pressure. The mechanical stimulation is characterized by non-linearity during the propagation. The positive peak pressure is above 0.1 MPa, more preferably 3 MPa, even more preferably at least 7 MPa, most preferably at least 15 MPa. The peak pressure in the positive maximum may be up to 150 MPa. The pulse duration of the mechanical stimulation (based on the time the pressure exceeds a half value of peak positive pressure) may be preferably in the range of hundreds of nanoseconds to tens of microseconds.

In comparing mechanical stimulation e.g. ultrasound and shock waves, not only are there differences in the shape and the propagation, but there are also significant differences between the physical effect of ultrasound and shock waves on the treated tissue, and particularly a cavitation effect. Cavitation is formation of gas bubbles in a fluid environment which occurs during the negative pressure wave in the liquid. Ultrasonic cavitation bubbles represent acoustic inhomogeneity in which incoming acoustic energy is absorbed and dissipated. Due to the high frequency of ultrasound waves, the acoustic energy may lead to rapid growth of cavitation bubbles and later to inertial cavitation effects, with breakup of the bubbles and violent damage of the surrounding tissue. Shock waves can reduce cavitation and the violent break up of cells resulting from cavitation.

The repetition rate (frequency) of the mechanical stimulation may be in the range from 0.1 Hz to 100 Hz, more preferably in the range from 0.5 to 50 Hz, most preferably in the range from 1 Hz to 40 Hz.

Four main principles for generating shock waves are described: electrohydraulic, piezoelectric, electromagnetic and pneumatic including ballistic. The shock waves produced by spark discharge, piezoelectric principle or electromagnetic principle are traditionally used for destruction of calculi e.g. kidney stones and based on its propagation it is possible to summarize them as focused. Electrohydraulic, piezoelectric and electromagnetic methods are also sometimes referred as hard shock waves because the energy is directed into small point in the tissue. On the other hand the electrohydraulic, piezoelectric, electromagnetic principle may be suitable if they are non-focused/radial, planar or moderately focused, and therefore softened.

Shock waves have a naturally non-focused/radial, planar or moderately focused propagation. Non-focused/radial, planar shock waves are characterized by smooth/soft propagation and therefore are preferred. The pneumatic principle of generating mechanical stimulation may be performed by pressurized gas vibrating a percussion guide or by ballistic shock waves which may be generated by striking of a bullet inside a guiding tube to a percussion guide. The bullet may be accelerated by pressurized gas, electric field, magnetic field, spring or other technique.

Also other principles (e.g. electrohydraulic, piezoelectric and electromagnetic) for generating non-focused, radial or moderately focused mechanical stimulation may be used. Moderate focus means varying levels of focused ultrasound energy or focal point in a distance longer than the treated tissue extends, where the energy in the focal point is not sufficient to cause harm of tissue.

Mechanical stimulation may be focused by reflectors, piezoelectric sources (mainly by their position and/or shape), or by using one or more focusing lenses. Focusing of the mechanical stimulation may also be provided by the shape of a percussion guide.

In order to achieve the best results in the soft tissue, the energy flux density of the mechanical stimulation is preferably in the range between 0.001 mW·mm$^{-2}$ and 160 mW·mm$^{-2}$, more preferably in the range between 0.001 mW·mm$^{-2}$ and 100 mW·mm$^{-2}$, most preferably in the range between 0.001 mW·mm$^{-2}$ and 50 mW·mm$^{-2}$.

Electromagnetic field used for heating the soft tissue may be radiofrequency field or microwave field, typically in the range of 0.1 MHz to 25 GHz, more preferably in the range from 0.1 MHz to 435 MHz, most preferably in the range from 0.1 MHz to 28 MHz. All the above mentioned waves may cause movement of charged particles e.g. ions, rotation of dipolar molecules or polarization of normally non polar particles and therefore increase the tissue temperature.

The device for proposed therapy may include a bipolar electrode system, where electrodes alternate between active and return function and where the thermal gradient beneath electrodes is almost the same during treatment. Bipolar electrodes may form circular or ellipsoidal shapes, where electrodes are concentric to each other. However, a group of bipolar electrodes may be used as well. Alternatively, a monopolar electrode system may be used. With the monopolar arrangement, the return electrode has a sufficiently large area in comparison to active electrode. The return electrode is in contact with skin of the patient and may by positioned relatively farther from the active electrode. A unipolar electrode may also optionally be used. Both capacitive and resistive electrodes may be used. Optionally one or more inductive electrodes may be used.

One or more multipolar electrodes may be used.

Figure 5A:
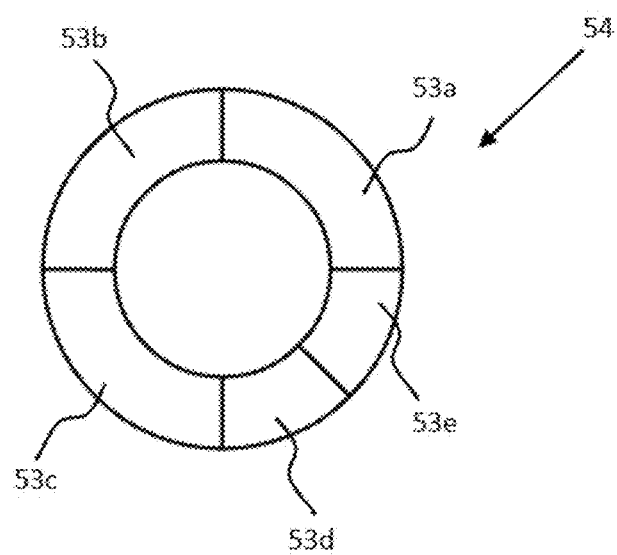
FIG. 5A is a schematic view of a multipolar electrode
Figure 5B:
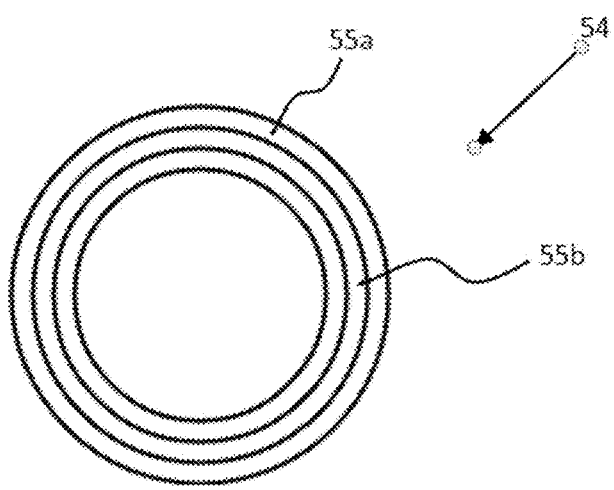
FIG. 5B is a schematic view of another multipolar electrode.

An energy delivery element may be divided into segments to provide treatment of selected parts of the tissue with higher efficiency or in a repeating manner. FIG. 5A shows energy delivery element divided to two or more segments 53a-d having the shape of an arc. A negative or positive charge of each segment may alternate. Each segment may be operated independently of other segments. Angular sections of the arc may be in the range of 1° to 359° or 5° to 275° to 15° to 185° or 20° to 95°. FIG. 5B shows energy delivery 54 divided to two or more segments 55a-d having the shape of layer, which may be concentric to each other.

In order to increase deep tissue heating by the electromagnetic field, the distance between electrodes may be varied; the electromagnetic field may be phase shifted or modulated; or an external magnetic field may be applied.

The electromagnetic field may be represented by light generated by one or more light sources. The wavelength of the light may be approximately in the range of 190 nm to 13000 nm or 350 nm to 2500 nm or 400 nm to 2000 nm. Applied light may be monochromatic or polychromatic. Light may be applied in pulses with pulse duration in the range of 0.1 μs to 10000 ms, more preferably in the range of 1 μs to 5000 ms, even more preferably in the range of 2 μs to 2500 ms, most preferably in the range of 5 μs to 1000 ms. Light may be applied close to specific spectral band. Term "close to" refers to deviation of 20%, more preferably 15%, most preferably 10% from the nominal wavelength. Applied spectral bands may be close to 405 nm, 450 nm, 530 nm, 560 nm, 575 nm, 640 nm, 685 nm, 830 nm, 915 nm, 1064 nm, 1280 nm, 1715 nm. Energy flux provided by light may be in the range of 0.005 W·cm$^{-2}$ to 500 W·cm$^{-2}$, more preferably in the range of 0.01 W·cm$^{-2}$ to 150 W·cm$^{-2}$ and most preferably in the range of 0.01 W·cm$^{-2}$ to 120 W·cm$^{-2}$. Spot size, which is defined as surface of tissue treated by the light, may be in the range of 0.01 cm$^2$ to 2000 cm$^2$, more preferably in the range of 0.05 cm$^2$ to 1500 cm$^2$, most preferably in the range of 0.1 cm$^2$ to 850 cm$^2$. The emission output power of the light source may be in the range from about 1 mW to about 150 W.

According to another embodiment, the electromagnetic field may be represented by near infrared waves generated by at least one laser diode module or LED approximately in the range from 600 nm to 1200 nm, more preferably from 630 nm to 990 nm. The emission output power of the laser diode module or LED are in the range from about 10 mW to about 10 W.

Energy flux density of the electromagnetic field is preferably in the range between 0.01 mW·mm$^{-2}$ and 10 000 mW·mm$^{-2}$, more preferably in the range between 0.1 mW·mm$^{-2}$ and 5 000 mW·mm$^{-2}$, most preferably in the range between 0.5 mW·mm$^{-2}$ and 1 000 mW·mm$^{-2}$.

The sum of energy flux density of the mechanical stimulation and electromagnetic field applied to the patient simultaneously, successively or in overlap should be preferably above 0.1 mW·mm$^{-2}$, 1 mW·mm$^{-2}$, or 5 mW·mm$^{-2}$, generally up to a maximum of 100, 500 or 1000 mW·mm$^{-2}$.

Cooling may be provided to the treated and/or untreated tissue. Cooling may be provided by any known mechanism including water cooling, sprayed coolant, presence of the active solid cooling element (e.g. thermocouple) and also by air flow.

The treatment device may include a transmatch adjusting impedance to the impedance of the treated tissue in order to maximize the power transmission. The transmatch may adjust the impedance in order to minimize the reflected power. The device may also include a balun transformer, which may be part of the transmatch. The balun may allow for treatment without need of grounding.

Figure 2:
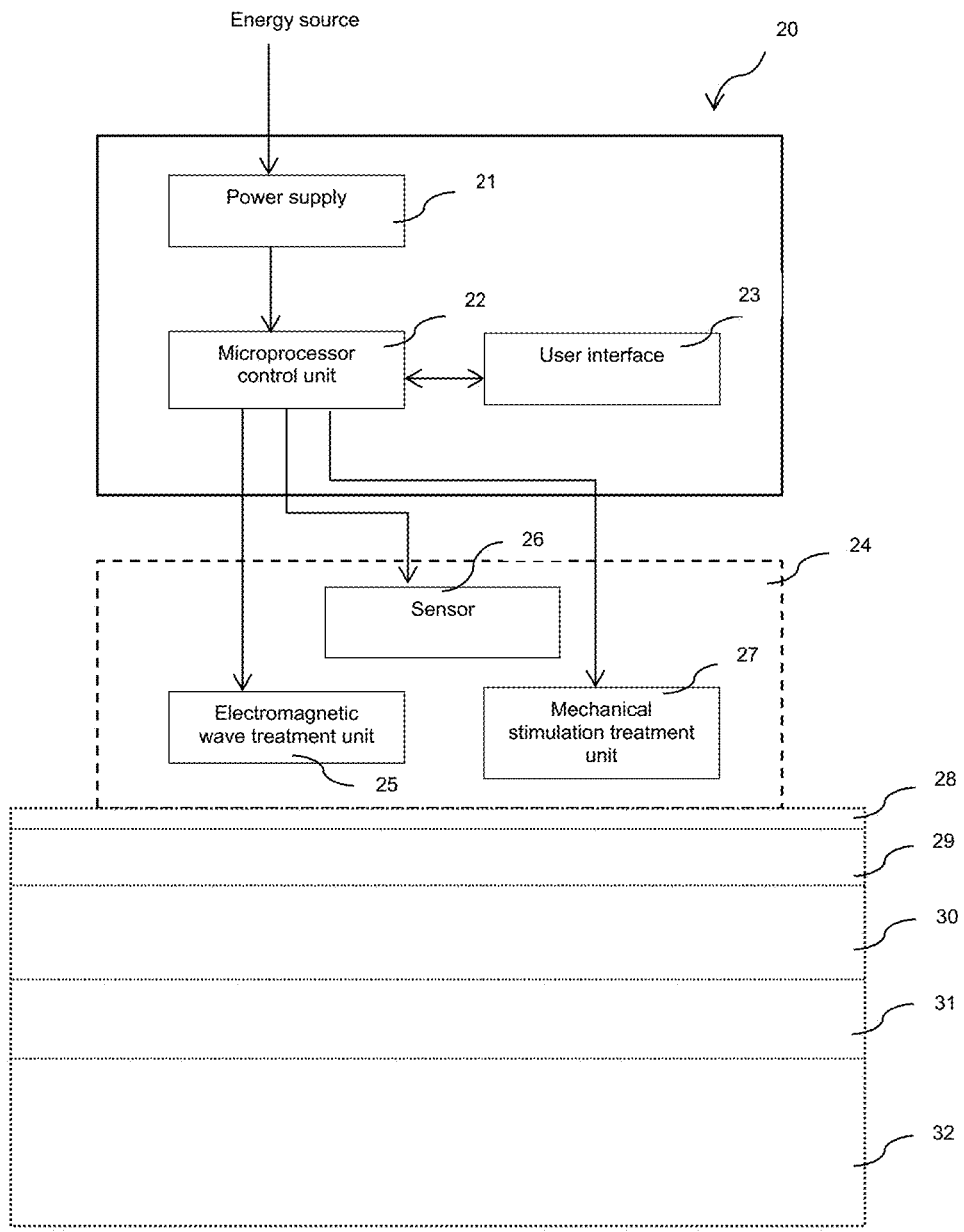
FIG. 2 is a schematic drawing of positioning of the system for skin treatment

FIG. 2 shows schematic example of positioning of the system for skin treatment. The system for skin treatment 20 applies a combination of electromagnetic and mechanical stimulation energy into the soft tissue. The system may include a power supply 21 connected to an energy source. The system for skin treatment 20 includes at least one applicator 24 which may be placed inside a case or may be separated from the system for skin treatment 20 and connected by a cable. The microprocessor control unit 22 with user interface 23 provides communication between the electromagnetic field treatment unit 25 and mechanical stimulation treatment unit 27. User interface 23 allows setting up the treatment parameters and also may provide the operator various treatment information. User interface 23 may include display. The electromagnetic field treatment unit 25 and mechanical stimulation treatment unit 27 may be placed in at least one applicator 24. However the treatment units may also have separate applicators. The applicator 24 may preferably contain a sensor unit 26

The output power of the power supply 21 may be in the range of 10 W to 600 W, preferably in the range of 50 W to 500 W, most preferably in the range of 80 W to 450 W.

The sensor unit 26 may contain one or more sensors for sensing temperature, resistance, movement, contact with skin or force applied to skin. The sensor may be invasive or contactless. The sensor may measure one or more physical quantities of the treated tissue and/or untreated tissue.

The temperature sensor measures and monitors the temperature of the treated tissue. Temperature can be analyzed by a microprocessor control unit 22. The temperature sensor may be a contact sensor, contactless sensor (e.g. infrared temperature sensor) or invasive sensor (e.g. a thermocouple) for precise temperature measuring of deep layers of soft tissue. The microprocessor control unit 22 may also use algorithms to calculate the deep or upper-most. A temperatures feedback system may control the temperature and based on set/pre-set limits, alert the operator in human perceptible form e.g. on the user interface 23. In a limit temperature condition, the device may be configured to adjust output power, activate cooling or stop the therapy. Human perceptible form may be sound and/or change of color of the applicator 24 and/or the tip.

A resistance sensor may measure the skin resistance, since it may vary for different patients, as well as the humidity, wetness and sweat may influence the resistance and therefore the behavior of the skin to electromagnetic field. Based on the measured skin resistance, the skin impedance may also be calculated.

The contact and/or force applied by the applicator on the skin surface may be measured piezoresistively, mechanically, optically, electrically, electromagnetically, magnetically or by other attitudes. The measured information from the contact and/or force sensor may influence the start of the therapy or generation of electromagnetic or mechanic field by treatment units. Information about the contact and/or force applied on the skin surface may be presented in human perceptible form to the operator.

Information from one or more sensors may be used for generation of a pathway on a convenient model e.g. a model of the human body shown on the display. The pathway may illustrate a surface and/or volume of already treated tissue, presently treated tissue, tissue to be treated, and/or untreated tissue. A convenient model may show a temperature map of the treated tissue providing information about the already treated tissue or untreated tissue.

The sensor may provide information about the location of bones, inflamed tissue and/or joints. Such types of tissue may not be targeted by mechanical stimulation due to the possibility of painful treatment. Bones, joints and/or inflamed tissue may be detected by any type of sensor such as an imaging sensor (ultrasound, IR sensor), impedance sensor and the like. A detected presence of these tissue types may cause generation of human perceptible signal, interruption of generation of electromagnetic energy and/or mechanical stimulation energy. Bones may be detected by a change of impedance of the tissue and/or by analysis of reflected mechanical waves and/or electromagnetic waves.

The system for skin treatment 20 generates electromagnetic waves and mechanical stimulation enabling improvement of the soft tissue, mainly connective tissue in the skin area. The connective tissue in the skin area contains layer epidermis 28 and dermis 29; white adipose tissue in hypodermis 30 and peritoneal cavity 32. The other soft tissue below the skin area e.g. muscular tissue 31 remains untreated and unharmed. The therapy may stimulate the blood circulation or may also create micro-disruptions of treated tissue, and/or create movement, rotation or polarization of particles by induced current and/or magnetic field which increase the temperature of treated tissue. The combined therapy may result in increased cell membrane permeability, which may result in increased liquefying of fat and/or lipolysis. Combination of both therapies highly reduces the risk of adipocytes inflammation.

Without being bound to the theory, it is believed that the mechanical stimulation may increase the penetration depth and enable remodeling of the visceral white adipose tissue which is located in the peritoneal cavity 32. The mechanical stimulation, in combination with electromagnetic field, may result in reduction of visceral fat cells. Therefore the overall number and/or volume of SWAT and/or VWAT may be reduced. Temperature of the treated tissue during the therapy may be increased to about 32-48° C.

Also neovascularization may be induced based on increased angiogenic grow factors VEGF, and also PCNA, NOS etc. Improvement of microvascular network may also result in better lipid metabolism functionality.

Another soft tissue improvement is in the field of tissue elasticity. The micro-disruptions also lead to improved tissue regeneration and in combination with electromagnetic field therapy induces neocollagenesis, neoelastogenesis and improvement of tissue elasticity. Although neocollagenesis is normally induced at higher temperatures than 32-48° C., the combination of mechanical stimulation and electromagnetic field enables improved results at temperatures in this range, resulting in less stress of the tissue. The treatment may include at least partial destruction and subsequent repair and/or synthesis of other forms of connective tissue, e.g. fibronectin, matricellular protein etc.

Transfer of the energy may change attributes of the tissue. Temperature of the tissue may be increased to about 32-48° C.

Methods may include direct contact of the applicator 24 with the tissue which may result in a deflection of the tissue by the applicator. The deflection may be in the range of 0.01 mm to 30 mm or 0.01 mm to 20 mm or 0.05 to 10 mm.

The direct contact of the applicator 24 with the tissue may form a recess in the tissue during treatment. The recess may be in the range of 0.001 cm to 8 cm or 0.01 cm to 6 cm or 0.05 to 4 cm or 0.01 cm to 3.5 cm.

The electromagnetic field and mechanical stimulation may be applied with a frequency ratio which provides significant results, convenient treatment and minimal adverse effects. The ratio between the electromagnetic field frequency and mechanical stimulation frequency (MHz/Hz) may be in the range of 0.005 to 60 or 0.01 to 28.

The mechanical stimulation also have an analgesic and myorelaxative effects which increase the comfort of therapy.

Treatment may be performed on the whole surface of the body or it may include particular parts of body e.g. face, neck, breasts, shoulders, thorax, abdomen, waistline, region of love handles, sides of the torso (e.g. bra fat), arms, buttocks, saddlebag, thighs, and calf. Treatment of the breasts may include treatment of the Cooper ligament. The present method and device may be used for treatment of sexual problems e.g. erectile dysfunction. Treatment may be targeted to the cavities of the body e.g. mouth, vagina and anus.

In another embodiment, the device may include a suction unit. The suction unit provides a vacuum or negative pressure on the treated skin. The suction unit may improve the contact mechanical stimulation treatment unit and/or electromagnetic field treatment unit with the skin surface and ensure better therapy.

The arrangement of mechanical stimulation treatment unit 27 and electromagnetic wave treatment unit 25 may be in one or more separate applicators 24. Where one applicator is used, the applicator 24 may contain one treatment energy delivery element designed for transmission of mechanical stimulation and electromagnetic waves into the soft tissue. However, the mechanical stimulation treatment unit 27 and electromagnetic wave treatment unit 25 may be designed with separate energy delivery elements organized in concentric, axial symmetrical or non-symmetrical ways.

Applicator 24 includes surface contacting the tissue including one or more energy delivery elements transmitting electromagnetic waves and one or more energy delivery element designed to transmit mechanical stimulation. The surface of a first energy delivery element is designed to transmit electromagnetic waves and a surface of a second energy delivery element is designed to transmit mechanical stimulation. The effective surface areas of the first and second energy delivery elements may have different ratios. The surface of first energy delivery element designed to transmit electromagnetic waves may cover at least 20%, more preferably 30%, still more preferably 35% and more preferably 40% of the applicator's surface contacting the tissue. The surface of second energy delivery element designed to transmit mechanical stimulation may be described as percussion guide.

The surface of the second energy delivery element may be at least 0.03 $cm^2$, or in the range of 0.05 $cm^2$ to 50 $cm^2$, more preferably in the range of 0.75 $cm^2$ to 40 $cm^2$, most preferably in the range of 0.1 $cm^2$ to 35 $cm^2$.

Surfaces of energy delivery elements providing electromagnetic field and mechanical stimulation may be in the different ratio, which was found to deliver most of the energy used for treatment. The ratio of the surface of the first energy delivery element providing the electromagnetic field to the surface of the second energy delivery element providing mechanical stimulation may be in the range of 0.01 to 80 or 0.05 to 65 or 0.1 to 50 (with the surface areas referring to the surface area of each element intended to make contact with the skin).

Movement of one or more applicators 24 may be provided by a robotic system, which may be controlled by the operator using the user interface 23. The robotic system may be also operated in automated manner, which may be guided in a pathway provided by a sensor.

Figure 6:
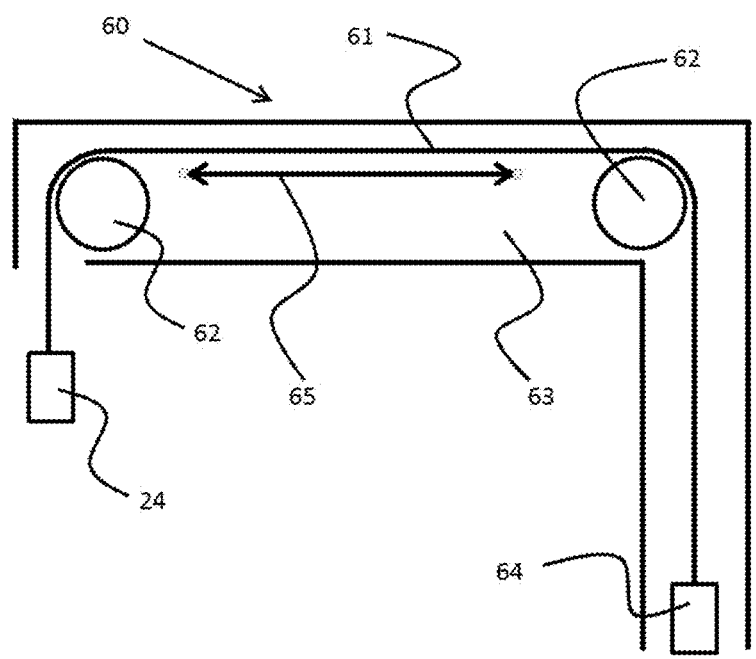
FIG. 6 is a schematic drawing of a system for moving an applicator.

FIG. 6 shows a device including an assisting movement element 60 which may increase and/or decrease the pressure applied on the tissue by the applicator 24 and/or device. Assisting movement element 60 may be used with manual movement of the applicator 24 to provide comfortable operation. Assisting movement element 60 may include one or more flexible link 61, sheaves 62 and/or movement elements 64 providing easier control to the applicator 24. Flexible link 61 and sheave 62 are shown to be located in the guiding element 63. Rope 61 may be moved in directions of the arrow 65. Forward movement of the flexible link 61 may increase the pressure applied by the applicator 24 on the tissue. Backward movement of the flexible link 61 may be enhanced by movement element 64 providing decreased weight of the applicator. Both these types of movement may be enhanced by movement element 64. Treatment may include combination of both movements in order to provide sufficient pressure and/or reduced fatigue of the operator by decreased weight of the applicator.

The methods and device described may provide an overall solution for soft tissue treatment, mainly in skin region including reduction in size and or volume of fat cells. The therapy also enables improvement of cellulite. The cellulite may be treated preferably without shrinkage of collagen fibers, since the triple helix structure is not denatured. Instead the method and system cause only micro-disruption at increased temperatures in the range 32-48° C. which increases the repair processes and collagen deposition.

Figure 3A:
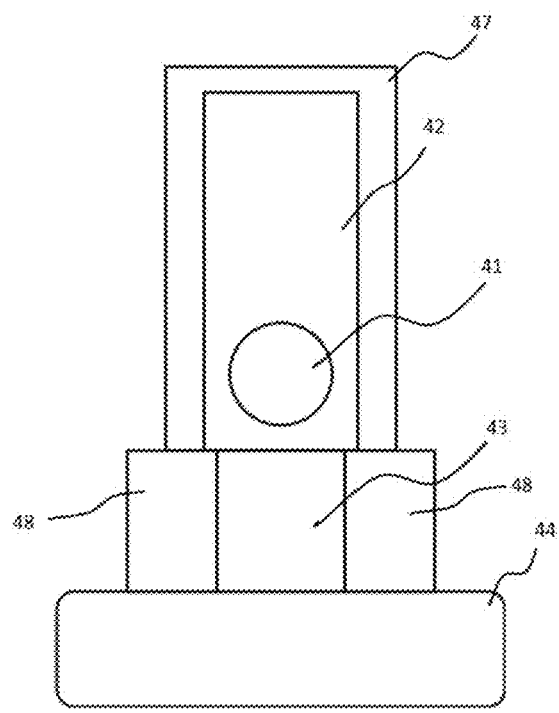
FIG. 3A is a schematic cross section of an applicator.
Figure 3B:
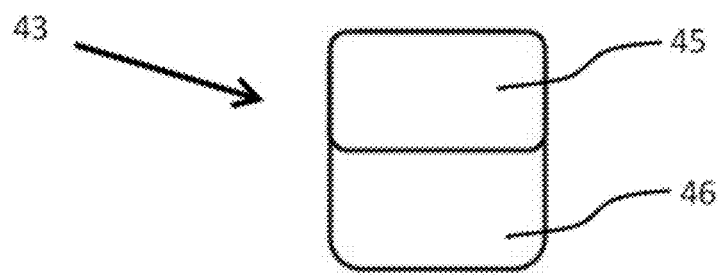
FIG. 3B is a schematic drawing of a percussion guide.

The method and device also provide treatment of dermatitis, atrophic disorders (e.g. stretch marks), wrinkles, dimpled skin, and/or hypertrophic disorders (e.g. scar). While analgesic effects of mechanical stimulation may provide dermatitis patient with relief of pain or itching, radiofrequency may provide heat causing at least partial regeneration of the tissue, initiation of the immunological response and/or its enhancement. Stretch marks may be treated by causing micro-disruption of the connective tissue and subsequent synthesis of new connective tissue. The method and device may also provide circumferential reduction, pain relief, body contouring, enhancement of lymphatic drainage, wound healing, enhancement of hyperaemia, improvement of microcirculation, improvement of vascularization, improvement of blood flow, skin tightening, rejuvenation of skin, tightening of lax skin (e.g. after liposuction), improvement of skin elasticity. Enhancement of skin hydration and/or removal or correction of pigment deficiencies, FIG. 3A shows exemplary cross section of applicator operated on ballistic principle including a bullet 41 inside a guiding tube 42 (enclosed in casing 47) striking to the percussion guide 43 representing an energy delivery element designed to transmit mechanical stimulation. Electrode 48 represents an energy delivery element designed to transmit electromagnetic waves. Generated mechanical stimulation is transmitted to the tissue 44. Percussion guide 43 may be constructed as one piece and it may include impact part 45 and tissue-facing part 46 (shown of FIG. 3B). In another embodiment percussion guide 43 may be divided into impact part 45 and tissue-facing part 46, wherein both parts have different characteristics. Impact part 45 may be embedded into tissue-facing part 46 and vice versa. Impact part 45 may be part of the guiding tube 42. More than one percussion guide 43 may be used.

The applicator and/or energy delivery elements (e.g. electrode 48 and/or percussion guide 43) may be detachable. Detaching these elements may ease cleaning the coupling medium (e.g. gel), used to transfer of the electromagnetic field and mechanical stimulation, from the system. Excess coupling medium may build up in a space between the percussion element 43 and electrode by movement of the applicator. Therefore, detaching these parts may provide a more reliable way of cleaning the system. The electrode 48 and/or percussion guide 43 may be detachable from the rest of the applicator. Optionally only electrode 48 or percussion element 43 may be detachable from the applicator 24.

Alternatively, the electrode 48 and percussion element 43 may be provided as one part of the device. In this case, the resulting element has characteristics of a percussion element and an electrode, therefore heating may be provided by the same surface delivering mechanical stimulation. Such configuration may prevent the disposition of the coupling medium on the applicator.

The system may also recognize the attached percussion element 43 and/or electrode 48 and allow only predefined treatments and/or set safety limits of the treatment related to the attached percussion element 43 and/or electrode 48.

The applicator may include a reservoir of medium (e.g. fluid and/or gel) for transferring mechanical stimulation. The reservoir may be located between tissue-facing part 46 of the percussion guide 43 and the wall contacting the tissue. Optionally, the applicator may include an assembly of two or more percussion guides transferring mechanical stimulation to the tissue through the reservoir. The reservoir may be detachable.

Percussion guide 43, impact part 45 and/or tissue-facing part 46 may be made from variety of materials e.g. metal, polymer, ceramic, glass, and/or natural material (e.g. bone, wood etc.). Furthermore, impact part 45 and/or tissue-facing part 46 may be made from different materials. Metals used may be titanium, chromium, manganese, aluminum, cobalt, vanadium and/or alloys. Such alloy may be e.g. stainless steel, Inconel, Nimonic and the like. Polymer may be thermoplastic polymer (e.g. polyurethane), polyepoxides, acrylate polymers, fibre-reinforced polymer (e.g. polyoxymethylene, carbon fiber reinforced polymer), and/or fluoropolymer. In another exemplary embodiment polymer may be Kevlar, rubber or silicone. Ceramic may be sintered ceramic.

Percussion guide 43 and/or its parts may be made of biocompatible composite coated with nanoparticles e.g. nano-carbon particles. Composite material may be e.g. ceramic, hydroxyapatite, fullerenes, carbon fiber reinforced polymer etc.

Percussion guide 43, impact part 45 and/or tissue-facing part 46 may be coated and/or covered by a layer of any of the materials mentioned above, and/or by any polymer (e.g. fluorocarbons), metal and/or vitreous enamel. A covering layer may be detachable from the percussion guide 43 and/or its parts.

One or more sensors may provide information about the temperature, shape and/or position of the percussion guide 43. The position of the percussion guide 43 may be changed by the striking of the bullet 41. When the bullet 41 changes the secured position of the percussion guide 43 in the guiding tube 42, the system may alert the operator in human perceptible form e.g. on the user interface 23. The system may also receive information about the state of the percussion guide 43, e.g. the number of strikes by the bullet 41. Based on such information, system may calculate the estimated number of future strikes of the bullet 41 and inform the operator about estimated lifetime of the percussion guide 43. The system may inform the operator by any human perceptible form.

Percussion guide 43, impact part 45 and/or tissue-facing part 46 may have any shape. Percussion guide 43 may have ellipsoidal or cylindrical shape with one or more recess. The impact part 45 may have a greater dimension than the tissue-facing part 46 causing increased pressure on the tissue providing a more focused effect. Optionally, the impact part 45 may have smaller dimensions than the tissue-facing part 46 providing decreased pressure and a more distributed effect. The tissue-facing part 46 may have a concave, convex and/or flat surface contacting the tissue. Concave surfaces and variations of the dimension of such shape may provide control of focus and/or penetration depth of the mechanical stimulation. Flat and/or convex surfaces may provide defocused and/or radial mechanical stimulation.

Percussion guide 43 and/or at least one of its parts may be cooled and/or heated, as controlled by the microprocessor control unit 22. Heating and/or cooling of the percussion guide 43 may influence the characteristics of transmitted mechanical stimulation and/or the temperature of the electrode 48 transmitting electromagnetic energy.

Figure 3C:
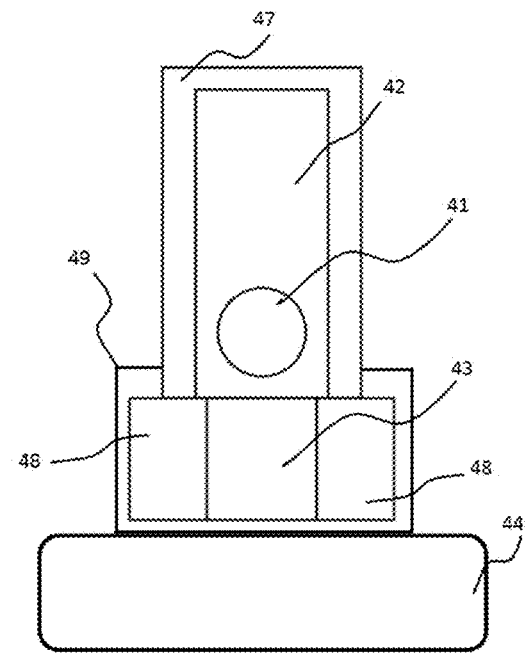
FIG. 3C is a schematic cross section of another applicator.

Applicator 24 may be covered by a protective sheath 49 shown on FIG. 3C during the treatment. The protective sheath 49 may be made of polymer and/or natural fibers. The protective sheath may separate applicator 24 from the tissue, protecting the applicator from disposition of an excess of the coupling medium. In another embodiment the protective sheath may separate apparatus from the coupling medium applied on the tissue. The protective sheath may be disposed after the treatment.

Treatment of soft tissue may be provided without using the coupling medium. Applicator 24 may include percussion guide 43 or tissue-facing part 46 having a smooth surface, which is made of and/or coated with polymer e.g. polytetrafluoroethylene. The treated tissue may be covered by material providing smooth surface for the movement of the applicator 24.

The bullet 41 in the guiding tube 42 may be accelerated by the pressurized gas. Gas may be pressurized by pressure in the range of 0.1 bar to 50 bar, more preferably in the range of 0.2 bar to 45 bar, most preferably in the range of 0.5 to 35 bar.

Soundproofing elements may be used for reducing the noise generated by the operation of the system. One soundproofing element may be an isolation tube positioned around the guiding tube 42 and/or the percussion element 43. Hence, the isolation tube may form isolation space around the mechanical stimulation treatment unit 27 and be a part of applicator 24. Isolation space may separate guiding tube 42 and/or percussion element 43 from the rest of the device by a layer of isolation material e.g. air, gas, solid substance and/or gel. Solid substances possessing soundproofing characteristics and elasticity may be e.g. silicone, melamine foam, melamine and/or resin. In still another embodiment the device may include one or more sensors providing information which may be used for analysis of the noise. The isolation space may include one or more elements providing destructive interference to the noise. According to one illustrative embodiment, protective sheath 49 may also have function of the soundproofing element.

Briefly stated, a method for soft tissue treatment of a patient includes positioning an applicator adjacent to the soft tissue of the patient; transmitting mechanical stimulation into the soft tissue of the patient causing mechanical stimulation of the soft tissue of the patient; transmitting electromagnetic waves from the applicator into the soft tissue with the electromagnetic waves heating the soft tissue; and remodeling soft tissues via the combination of mechanical stimulation and electromagnetic waves. The method may remodel the soft tissue and cause reduction of the VWAT and/or the SWAT; reduction in the number of adipose cells; reduction in the volume of adipose cells; and/or improve connective tissue elasticity or cellulite appearance. The method may also improve elasticity of fibrous septae connecting the dermis to underlying fascia.

Methods of treatment may include stimulation of flow of the lymph through the lymphatic system providing faster transfer of remnants of lipolysis. The weight of the applicator, reinforced by assisting movements, together with proper movement of the applicator may increase the velocity of flow of the lymph through the lymph vessels. Proper movement of the applicator may be performed by the operator through direct or indirect control and/or by a robotic system. The applicator may be moved in continuous longitudinal movements, which may have any shape e.g. loop, circular and/or random. The applicator may be also moved in straight line. Movement of the applicator may be in the direction from the center of the treated part of the body to its periphery. Movement of the applicator may also be in the direction from the periphery of the treated part of the body towards the center of the body. Continuous movement may be directed to one or more lymph nodes e.g. lymph nodes in the groins. Treatment may enhance blood flow in the adipose tissue, which may lead to increased heat distribution to adjacent volumes of treated and/or untreated tissue.

Figure 4:
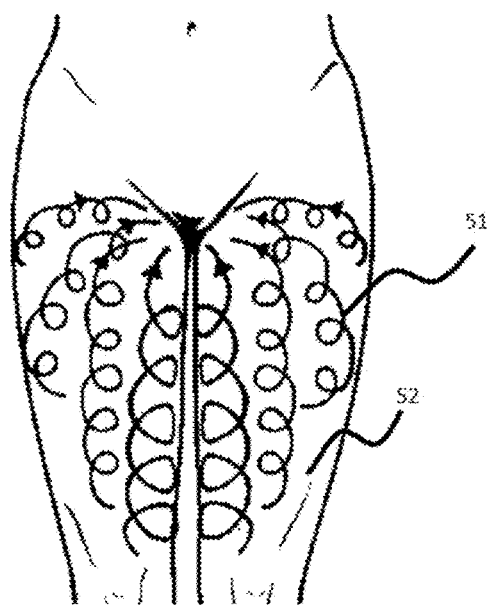
FIG. 4 is a schematic example of movement of the applicator.

The treatment may include straight or continuous circular movement of the applicator towards the lymph nodes in the groins. FIG. 4 shows an example of treatment of front thigh 52. The direction of movements 51 toward the groins may cause stimulation of lymph flow to the lymph node. The treatment of the abdomen may include movement of the applicator toward one or more lymph nodes located in the abdomen. The treatment of the arm may include straight or continuous circular movement of the applicator towards the lymph node located in the underarms. The treatment of the head may include straight or continuous circular movement of the applicator towards the one or more lymph nodes located in the head or neck e.g. a circular lymph node, parotid node, submental node, submandibular node and/or occipital node.

Thus, novel apparatus and methods have been shown and described. Various changes and substitutions may of course be made without departing from the spirit and scope of the invention. The invention, therefore, should not be limited except by the following claims and their equivalents.

The invention claimed is:

1. A method for treating adipose tissue of a patient comprising:
    positioning an applicator adjacent to tissue of the patient;
    pneumatically generating mechanical stimulation having a frequency in the range of 0.1 Hz to 100 Hz;
    transmitting the mechanical stimulation from the applicator into the adipose tissue of the patient causing mechanical stimulation of the adipose tissue of the patient;
    transmitting electromagnetic waves from the applicator into the adipose tissue with the electromagnetic waves heating the adipose tissue;
    remodeling the adipose tissue via the combination of mechanical stimulation and electromagnetic waves; and
    where a sum of energy flux of the mechanical waves and electromagnetic waves is in the range between 0.1 mW·mm$^{-2}$ and 1000 mW·mm$^{-2}$.

2. The method of claim 1 wherein the temperature of the adipose tissue is increased to about 32-48° C.

3. The method of claim 2 where the mechanical waves have a positive peak pressure greater than 15 MPa.

4. The method of claim 1 where electromagnetic waves comprise light having energy flux in the range of 0.005 W·cm$^{-2}$ to 500 W·cm$^{-2}$.

5. The method of claim 4 where the light has spot size in the range of 0.01 cm$^2$ to 2000 cm$^2$.

6. The method of claim 1 further including deflecting the tissue during the application of mechanical waves in the range of 0.01 mm to 30 mm.

7. The method of claim 1 where the adipose tissue is white subcutaneous adipose tissue.

8. A method for treating a tissue of a patient comprising:
    positioning an applicator adjacent to tissue of the patient;
    providing mechanical stimulation from the applicator into the tissue of the patient using a pneumatic device, with the mechanical stimulation at a frequency in the range of 0.1 Hz to 100 Hz;
    transmitting electromagnetic waves from the applicator into the tissue of the patient with the electromagnetic waves heating the tissue and increasing the temperature of the tissue to about 32-48° C.;
    remodeling the tissue via the combination of mechanical stimulation and electromagnetic waves;
    with the mechanical stimulation providing a massaging effect on the patient and wherein the electromagnetic waves are provided by a first energy delivery element having a first surface area, and the mechanical stimulation is provided by a second energy delivery element having a second surface area, and wherein a ratio of the first surface area to the second surface area is in the range of 0.01 to 80 and
    wherein the second energy delivery element contacts the tissue.

9. The method of claim 8 with the mechanical stimulation and electromagnetic field having a combined energy flux in the range of 0.1 mW·mm$^{-2}$ and 1000 mW·mm$^{-2}$.

10. The method of claim 9 where the mechanical stimulation has a positive peak pressure greater than 15 MPa.

11. The method of claim 8 where the electromagnetic waves comprise light having an energy flux in the range of 0.005 W·cm$^{-2}$ to 500 W·cm$^{-2}$.

12. The method of claim 11 where the light has a spot size in the range of 0.01 cm$^2$ to 2000 cm$^2$.

13. The method of claim 8 wherein the tissue is cellulite tissue.

14. The method of claim 8 further including moving the applicator towards a lymph node in the groin of the patient.

15. A method for treating a tissue of a patient comprising:
    positioning an applicator adjacent to tissue of the patient;
    providing mechanical stimulation from the applicator into the tissue of the patient using a pneumatic device, with the mechanical stimulation at a frequency in the range of 0.1 Hz to 100 Hz; transmitting electromagnetic waves from the applicator into the tissue of the patient with the electromagnetic waves heating the tissue and increasing the temperature of the tissue to about 32-48° C.; remodeling the tissue via the combination of mechanical stimulation and electromagnetic waves; where a sum of energy flux of the mechanical stimulation and electromagnetic waves is in the range of 0.1 mW·mm$^{-2}$ and 1000 mW·mm$^{-2}$; and circumferentially reducing a part of the patient.

16. The method of claim 15 where the mechanical stimulation and electromagnetic waves are provided by detachable energy delivery elements.

17. The method of claim 15 where the electromagnetic waves comprise light having energy flux in the range of 0.005 W·cm$^{-2}$ to 500 W·cm$^{-2}$.

18. The method of claim 17 where the light has a spot size in the range of 0.01 cm$^2$ to 2000 cm$^2$.

19. The method of claim 15 with the applicator creating a recess in the tissue in the range 0.001 cm to 8 cm.

20. The method of claim 19 where the recess is changed in the range of 0.001 mm to 30 mm by the application of the mechanical stimulation.

21. The method of claim 15 wherein the electromagnetic waves are provided by a first energy delivery element having a first surface area, and the mechanical stimulation is provided by a second energy delivery element having a second surface area, and wherein a ratio of the first surface area to the second surface area is in the range of 0.01 to 80 and
    wherein the second energy delivery element contacts the tissue.

22. A method for treating a dermal tissue of a patient comprising:
    positioning an applicator adjacent to tissue of the patient;
    pneumatically generating mechanical stimulation from the applicator in the range of 0.1 Hz to 100 Hz;
    and transmitting the mechanical stimulation into the dermal tissue of the patient causing mechanical stimulation of the dermal tissue of the patient;
    transmitting electromagnetic waves from the applicator into the dermal tissue with the electromagnetic waves heating the dermal tissue wherein the temperature of the dermal tissue is increased to about 32-48° C.;

remodeling the dermal tissue via the combination of the mechanical stimulation and the electromagnetic waves; and where the mechanical stimulation and electromagnetic waves have a combined energy flux in the range between 0.1 mW·mm$^{-2}$ and 1000 mW·mm$^{-2}$.

23. The method of claim 22 where the mechanical stimulation has a positive peak pressure greater than 15 MPa.

24. The method of claim 22 where electromagnetic waves comprise light having an energy flux in the range of 0.005 W·cm$^{-2}$ to 500 W·cm$^{-2}$.

25. The method of claim 24 where the light has spot size in the range of 0.01 cm$^2$ to 2000 cm$^2$.

26. The method of claim 22 where the electromagnetic waves and the mechanical stimulation have a frequency ratio of 0.005 to 60.

27. The method of claim 22 where the electromagnetic waves and the mechanical stimulation are provided by different energy delivery elements, wherein the energy delivery element providing the electromagnetic waves and the energy delivery element providing the mechanical stimulation have a surface area ratio in the range of 0.01 to 80.

28. The method of claim 22 with the applicator creating a recess in the tissue is in the range 0.001 cm to 8 cm.

29. The method of claim 22 further including moving the applicator in straight or continuous circular movement towards a lymph node in the groin of the patient.

* * * * *